United States Patent
Pitman

(10) Patent No.: US 9,707,398 B2
(45) Date of Patent: *Jul. 18, 2017

(54) TREATMENT OF SPASMODIC DYSPHONIA VIA NEUROMODULATION

(71) Applicant: Michael J. Pitman, New York, NY (US)

(72) Inventor: Michael J. Pitman, New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/620,071

(22) Filed: Feb. 11, 2015

(65) Prior Publication Data

US 2015/0151129 A1 Jun. 4, 2015

Related U.S. Application Data

(63) Continuation-in-part of application No. 13/854,031, filed on Mar. 29, 2013, now Pat. No. 9,095,707.

(60) Provisional application No. 61/938,627, filed on Feb. 11, 2014, provisional application No. 61/617,537, filed on Mar. 29, 2012.

(51) Int. Cl.
*A61N 1/36* (2006.01)
*A61N 1/05* (2006.01)

(52) U.S. Cl.
CPC ...... *A61N 1/36164* (2013.01); *A61N 1/36003* (2013.01); *A61N 1/36057* (2013.01); *A61N 1/0556* (2013.01); *A61N 1/3601* (2013.01); *A61N 1/3611* (2013.01)

(58) Field of Classification Search
USPC .................................................. 607/3, 48, 62
See application file for complete search history.

(56) References Cited

U.S. PATENT DOCUMENTS 8,838,252 B2 * 9/2014 Pitman ........................... 607/62
2013/0150908 A1 * 6/2013 Lindenthaler ..................... 607/3

* cited by examiner

*Primary Examiner* — Carl H Layno
*Assistant Examiner* — Jon Eric C Morales
(74) *Attorney, Agent, or Firm* — Schwabe, Williamson & Wyatt P.C.

(57) ABSTRACT

The present disclosure relates to methods and apparatus for the treatment of spasmodic dysphonia, such as methods of treating spasmodic dysphonia that include providing a system that includes a stimulating electrode operably connected with a processor configured to set one or more stimulation parameters for an electrical impulse deliverable by said electrode, placing the electrode in electrical contact with the superior laryngeal nerve, using the processor to set the stimulation parameters such that the electrical impulse causes a level of stimulation that does not exceed the excitability threshold of one or more alpha motor neurons located within the thyroarytenoid muscle; and delivering the electrical impulse to the superior laryngeal nerve.

18 Claims, 12 Drawing Sheets

POSTERIOR CRICOARYTENOID

THYROARYTENOID

LATERAL CRICOARYTENOID

INTERARYTENOID

CRICOTHYROID

US 9,707,398 B2

TREATMENT OF SPASMODIC DYSPHONIA VIA NEUROMODULATION

CROSS REFERENCE TO RELATED APPLICATIONS

This application is a continuation-in-part of and claims priority to U.S. application Ser. No. 13/854,031, which issued as U.S. Pat. No. 9,095,707, filed Mar. 29, 2013, entitled "METHOD AND APPARATUS FOR THE TREATMENT OF FOCAL DYSTONIA," which claims priority to U.S. Provisional Patent Application No. 61/617,537, entitled "METHOD AND APPARATUS FOR THE TREATMENT OF SPASMODIC DYSPHONIA," filed on Mar. 29, 2012; the present application also claims priority to U.S. Provisional Patent Application No. 61/938,627, filed Feb. 11, 2014 and titled "TREATMENT OF SPASMODIC DYSPHONIA THROUGH AFFERENT ELECTROMUSCULAR STIMULATION," the entire disclosures of which are hereby incorporated by reference in their entirety.

TECHNICAL FIELD

The present disclosure relates to methods and apparatus for the treatment of spasmodic dysphonia, for example, via neuromodulation.

BACKGROUND

The larynx serves multiple functions, including control of respiration, airway protection, coordination of swallowing, and phonation. During swallowing, the larynx closes the airway in order to prevent aspiration of food or liquid. During inhalation, the larynx must not occlude the airway, and during speech, it must be positioned in order to accomplish phonation. Moreover, speech requires extremely precise movements of the larynx.

Spasmodic dysphonia (SD) is a focal, action-specific dystonia of the laryngeal musculature during phonation. It has a profound effect on patients' productivity and quality of life. The standard treatment for SD is botulinum toxin (BTX) injection of the laryngeal musculature. Unwanted side effects of adductor muscle injections include the loss of phonatory volume, breathiness, and dysphagia; whereas those of abductor muscle injections include dyspnea due to airway compromise.

The injections are painful and must be repeated nearly every 3 months. Due to the delayed onset of BTX effects and increasing symptoms prior to repeat injection, optimal voicing is achieved during only 30% of the injection cycle.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1:
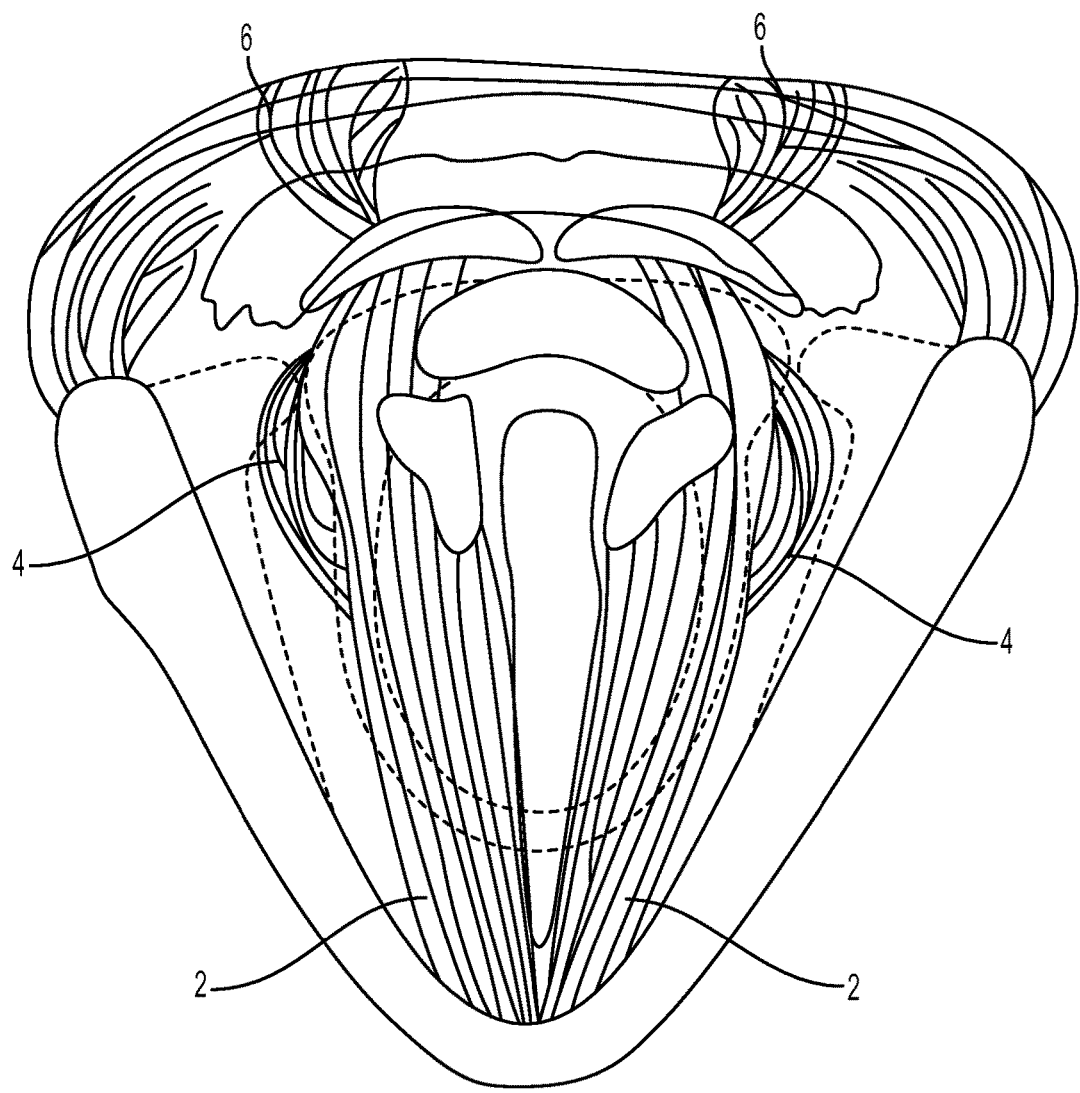
FIG. 1 illustrates a top view of the larynx.
Figure 2A:
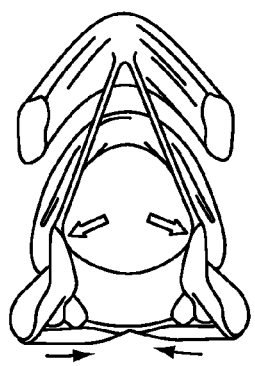
FIGS. 2A-2E illustrate five laryngoscopic views of the intrinsic muscles responsible for activating vocal cord position, including the posterior cricoarytenoid (FIG. 2A), the thyroarytenoid (FIG. 2B), the lateral cricoarytenoid (FIG. 2C), the interartytenoid (FIG. 2D), and the cricothyroid (FIG. 2E)
Figure 2B:
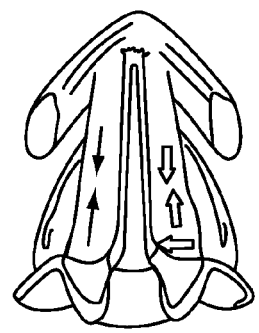
Figure 2C:
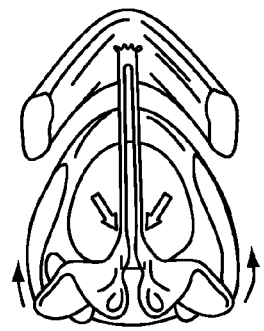
Figure 2D:
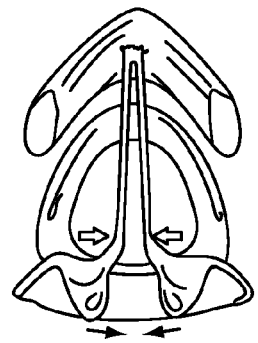
Figure 2E:
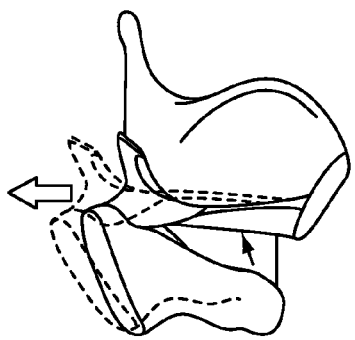

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide methods and apparatus for treating spasmodic dysphonia (SD) using neuromodulation. In particular, various embodiments are methods of treating SD that are based on the surprising finding that low-level electrical stimulation of a sensory nerve, the superior laryngeal nerve, alleviates symptoms of SD. Prior to the present disclosure, treatment methods instead focused on attenuation of motor neuron firing and/or the resulting muscular response.

SD is a disorder in which one or more laryngeal muscles spasm during phonation. SD manifests as a focal laryngeal dystonia affecting the control of vocal fold movements during phonation. It is a chronic, focal, movement-induced, action-specific dystonia of the laryngeal musculature during phonation. The condition makes speech very difficult for those affected, and consequently it is an isolating and even debilitating problem. SD may have a profound effect on quality of life, severely limiting people's communication, especially via telephone, during public speaking and in noisy backgrounds.

Two subtypes of this disorder have been identified. The first is adductor spasmodic dysphonia (ADSD), characterized by breaks in vowels attributable to thyroarytenoid (TA) muscle spasms resulting in intermittent hyperadduction of the vocal folds. The characteristic vocal breaks of adductor SD are due to spasmodic hyperadduction of the vocal folds that interrupt phonation. As a result of the force of the spasms, which generally occur with voiced vowels, vocal fold closure interrupts phonation, causing a strained or strangled vocal quality with intermittent vocal breaks.

The second subtype is abductor spasmodic dysphonia (ABSD), characterized by intermittent breathy voice and sudden pitch breaks. In ABSD, symptoms are thought to be due to spasms of the posterior cricoarytenoid muscles and, in some cases, the cricothyroid muscles. The incidence of prolonged vocal breathiness after voiceless consonants is thought to occur as a result of sustained vocal fold abduction due to the dystonic muscle spasm. ABSD is quite rare.

Historically, treatment of SD has been aimed at paralyzing or weakening one of the vocal folds in order to decrease its ability spasm and interrupt phonation. One such approach involved recurrent laryngeal nerve resection, or in some cases, crushing the recurrent laryngeal nerve to weaken the vocal folds but keep the nerve intact. Unfortunately, over the long term, the majority of patients who underwent either resection or nerve crush experienced a return of their phonatory spasms.

A number of other procedures were designed to decrease the strength of the vocal fold contraction. For example, type 2 laryngoplasty has been used for adductor SD. This procedure relaxes and lateralizes the vocal folds, and this anatomic alteration prevents the vocal fold spasm from forcefully obstructing airflow and causing a vocal break. However, if this procedure is overdone, a patient's speaking voice can be excessively raspy and breathy.

Another surgical approach to weaken the vocal folds to treat SD is bilateral thyroarytenoid and lateral cricoarytenoid muscle resection. Short-term results were promising, but long-term studies are needed, especially considering the failed history of performing myectomy for other dystonias, such as blepharospasm, which not only fails to prevent recurrence of symptoms, but often causes the muscle to become dysfunctional due to fibrosis and scarring.

The injection of botulinum toxin (BTX) into the larynx is the treatment of choice for adductor SD. It is believed that the BTX decreases the motor activity of the recurrent laryngeal nerve (RLN), inducing paresis of the vocal folds and thereby preventing phonatory interruption with vocal spasms, essentially performing a chemical neurectomy which denervates and weakens the muscles. The thyroarytenoid muscles are usually injected with BTX under electromyography (EMG) guidance via a cricothyroid membrane submucosal approach. The clinical effect of botulinum toxin in SD is classically thought to result from reducing the activity of the motor nerves, thereby weakening the laryngeal muscle and weakening its spasms.

Patients with SD who have had laryngeal injections of BTX may experience smoother speech with fewer voice breaks. However, the injections do not completely control symptoms, and the injections must be repeated approximately every three months. The procedure is painful, and immediately following an injection, patients experience side effects such as a weak voice. Prior to the next injection, patients' spasms return. As such, there is a sinusoidal symptom curve, and symptoms are optimally controlled for only a portion of the treatment cycle.

Historically, most applications of neuromuscular stimulation in the larynx have been aimed at reanimating paralyzed muscle to relieve laryngeal paralysis or paresis, rather than reducing muscle spasms to treat SD. Typically, neuromuscular stimulation intended to treat laryngeal paralysis acts on motor nerves to cause muscle contractions.

The nature of the functions of the larynx creates unique challenges to treatment through electrical stimulation. A high level of motor control of the muscles of the larynx is essential for airway protection during swallowing. The primary muscle, the thyroarytenoid muscle, is involved in rapid changes in vocal fold position for airway protection, swallowing, and speech. Rapid, precise changes in vocal fold adduction and abduction are required for voice production during speech, and less precise but rapid changes are required for cough and swallowing. Interference with normal muscular control of the larynx can interfere with these functions and cause inadequate protection of the airway, which can lead to aspiration of food, liquid, or saliva and aspiration pneumonia or even choking.

As disclosed herein, in various embodiments, targeted afferent electrical stimulation via the superior laryngeal nerve may effectively treat SD without resulting in potentially life-threatening complications, such as loss of motor control of the larynx or other undesirable effects that may occur as a result of undifferentiated electrical stimulation.

As discussed above, the general belief is that symptoms of SD result from abnormal motor signals to motor neurons which control the muscles of the larynx. FIG. 1 illustrates a top view of the larynx, and FIGS. 2A-2E illustrate five laryngoscopic views of the intrinsic muscles responsible for activating vocal cord position, including the posterior cricoarytenoid (FIG. 2A), the thyroarytenoid (FIG. 2B), the lateral cricoarytenoid (FIG. 2C), the interartytenoid (FIG. 2D), and the cricothyroid (FIG. 2E), all in accordance with various embodiments. Referring to FIGS. 1 and 2, the muscles of the larynx implicated in SD include the thyroartenoid 2, the interarytenoid, the cricothyroid, the lateralcricoarytenoid 4, and the posterior cricoarytenoid 6. Abnormal motor neural activity causes laryngeal muscles to spasm, resulting in a voice break and the symptoms of SD. Within this paradigm, it is assumed that BTX is effective because it interferes with the motor nerves innervating the muscle into which it has been injected, and thus interferes with the muscle's ability to spasm. According to this theory, the central nervous system continues to send abnormal motor signals to motor neurons, but they are unable to cause muscle contractions as forcefully.

However, electromyography has shown bilateral neuromuscular changes in the muscles of the larynx after unilateral BTX injection, which indicates that there is more benefit to BTX injection than simple weakening of the thyroarytenoid (TA) muscle. As disclosed herein, contrary to conventional thinking, SD is instead caused by abnormal afferent nerve signals, and not abnormal motor nerve signals.

Efferent nerves, also known as motor neurons, carry nerve impulses from the central nervous system to effectors such as muscles, and they are involved in muscular control. Afferent neurons, also known as receptor neurons, carry nerve impulses to the central nervous system. Signals carried by afferent nerves create sensations that the brain then identifies as pain, itch, stretch, etc.

In previous filings (e.g., U.S. patent application Ser. No. 13/854,029, filed Mar. 29, 2013, U.S. patent application Ser. No. 13/054,031, filed Mar. 29, 2013, and U.S. Provisional Patent Application No. 61/617,537, filed Mar. 29, 2012, all of which are incorporated herein by reference), methods were disclosed for the treatment of SD through sensory stimulation delivered by implantation of hooked wire electrodes into the TA muscle. Such stimulation was effective, but presented drawbacks.

Most of the muscle spindles located in the thyroarytenoid muscles are close to the attachment of muscle fibers to the vocal process of the arytenoid cartilage and near the attachment of the muscle, at the thyroid cartilage. In particular, the muscle spindles are positioned close to the medial border of the muscle, near the vocal ligament, as well as near the superior limit of the muscle. Because of that positioning, when electrodes are planted in the TA muscle, they may interfere with the intrinsic vibrational characteristics of the vocal fold. Moreover, induction of pain sensation when positioning electrodes in that location may occur because of the presence of the proprioceptive pain fibers located in the tendons of the muscles. Furthermore, positioning electrodes close to the TA muscle spindles reduces the stimulation target to a sub-group of all muscle spindles, thus generating only a partial TA stimulation.

Surprisingly, as disclosed herein, in various embodiments, more effective electrical stimulation may be delivered to the internal branch of the superior laryngeal nerve (SLN). This approach is contrary to conventional wisdom, as Ludlow, et al. (Muscle Nerve 2000; 23(1):44-57) indicated that chronic recurrent laryngeal nerve stimulation may cause nerve injury when a nerve cuff is used. As the SLN enters the endolarynx, by stimulating that trunk, it has been found that it is possible to induce the neuromodulation of all afferent nerve fibers of the larynx implicated in ADSD, as well as the afferent and gamma motor neuron nerve fibers of laryngeal muscle spindles simultaneously, while avoiding the need to position the electrodes in a muscular zone affected by high mechanical stress. In various embodiments, as compared to stimulation within the thyroarytenoid muscle, stimulation of the internal branch of the SLN as it enters the endolarynx affects more neurons, as the neurons are still aggregated in a small area, prior to their dispersion throughout the endolarynx.

In various embodiments, such electrodes may be placed using a minimally invasive, subcutaneous insertion location. Most importantly, in various embodiments, stimulation of motor nerves that converge into the endolaryngeal muscles may be minimized, thus avoiding the risk of interfering with motor neural activity necessary effectuate laryngeal functions such as airway protection.

Figure 3:
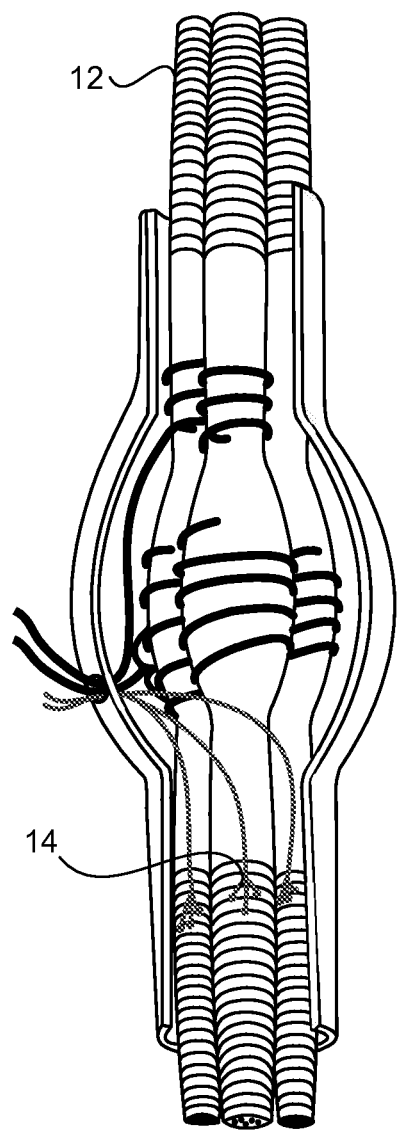
FIG. 3 is a cut away view of a muscle spindle.
Figure 4:
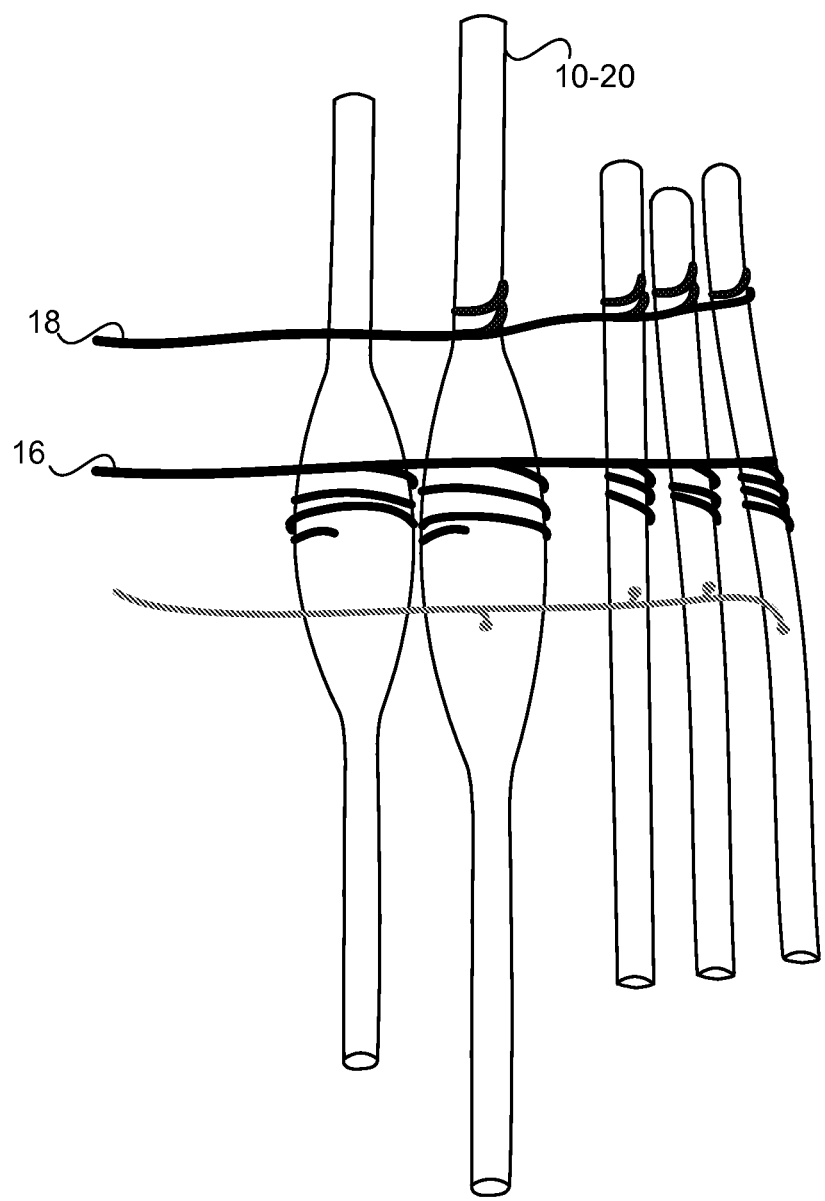
FIG. 4 is a cut away view of a muscle spindle.

As shown in FIGS. 3 and 4, muscle spindles 10 include both gamma motor neurons and afferent (sensory) neurons, and are an important component of muscular proprioception. The intrafusal muscle fibers 12, are innervated by type Ia 16 and type II 18 sensory afferent neurons. They lie parallel to the extrafusal muscle fibers and are innervated with afferent nerves, which sense muscle length and rate of changes in muscle length.

The gamma motor neuron 14 also innervates the intrafusal fibers 12 of the muscle spindle 10. By causing contraction of the intrafusal muscle fibers, the gamma motor neuron increases the sensitivity of the afferent neurons of the muscle spindle. When alpha neurons fire and cause the muscles to contract, the muscle spindles shorten and become slack, and lose their ability to detect muscle length. To prevent this, when the central nervous system sends signals via alpha neurons, co-activating signals are also sent to the gamma motor neurons 14. The gamma motor neurons maintain tautness of muscle spindles even as a muscle contracts, and permit the muscle spindles to detect muscle length. Gamma motor neuron activity is further modulated by input from the type Ia afferent nerve as it senses changes in muscle length and velocity. Thus, the gamma motor neurons set the sensitivity of muscle spindles.

The consistent level of gamma activity is called gamma bias. Overactive gamma motor neurons with a high bias result in hyper-sensitivity of the afferent nerves of the muscle spindle. As a result, muscle contractions are inappropriately increased, resulting in a muscle spasm.

As discussed above, it is generally believed that the symptoms of spasmodic dysphonia result from abnormal motor signals from motor neurons that control the muscles the larynx, and that abnormal motor neuron activity causes the muscles to spasm, resulting in SD. However, as described herein in various embodiments, contrary to the conventional thinking, spasmodic dysphonia is instead caused by abnormal afferent nerve signals and not abnormal motor signals. Abnormal afferent nerve signals that originate in the larynx cause abnormal motor signals, which in turn cause the muscles to spasm. BTX inhibits the function of motor nerves by preventing nerves from releasing acetycholine at the synaptic junction. Without being bound by theory, BTX may work on the gamma motor neurons in the muscle spindle in much the same way as it works on the alpha motor neurons, in that it decreases activity of both types of nerves via the same mechanism.

Neuromuscular stimulation, on the other hand, is often used to increase neurologic activity, in other words, cause muscles to contract, e.g., in order to treat paralysis or paresis. The use of neuromuscular stimulation to impact the afferent nervous system is different from the present disclosure in both objects and methodology. For example, it is well accepted that the application of electrical stimulation to a muscle will cause that muscle to contract when the stimulation rises above the excitability threshold of the innervating motor neurons. However, the effects of stimulation on the afferent system are less predictable. As disclosed herein, a relatively low level of electrical stimulation of the superior laryngeal nerve may modulate the gamma loop, reducing the gain of the muscle spindle and sensitivity of the Ia efferent nerve, causing a reduction in abnormal sensory signaling.

Figure 5:
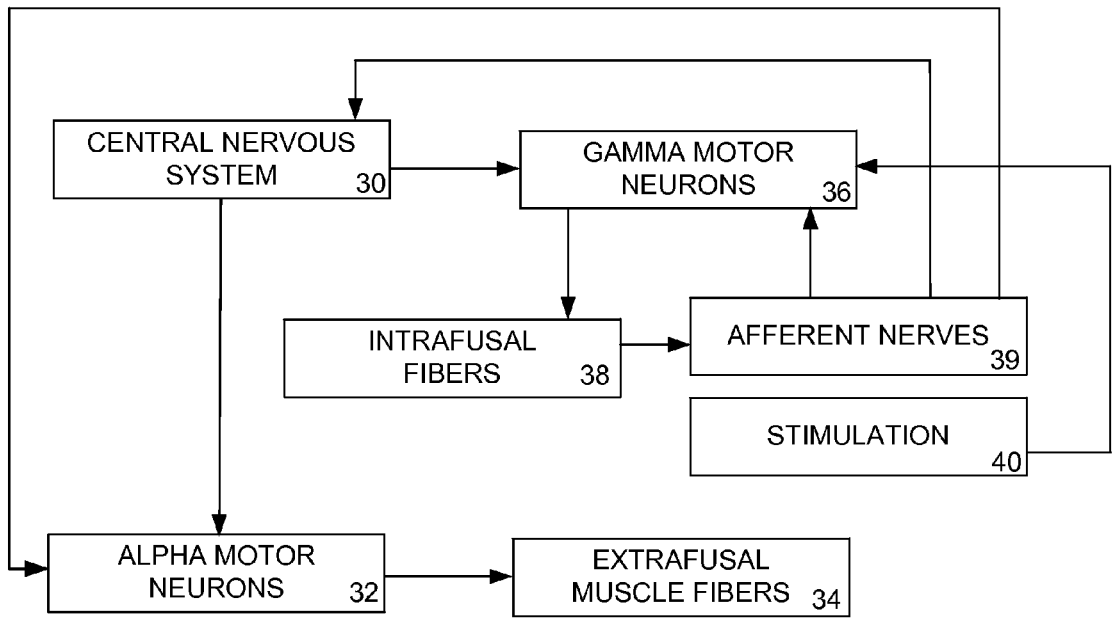
FIG. 5 is a flow chart illustrating the direction of impulses communicated between the central nervous system, the motor neurons, the muscles, the afferent nerves, and the gamma neurons and the impact of stimulation on gamma motor neurons.

As shown in the example illustrated in FIG. 5, the central nervous system 30 sends impulses to alpha motor neurons 32, which act on extrafusal muscles fibers 34. The central nervous system simultaneously sends impulses to the gamma motor neurons 36, which act on the intrafusal muscle fibers 38 of the muscle spindles. The gamma motor neurons 36 are coactivated with the alpha motor neurons 32 to maintain an appropriate level of sensitivity in the muscle spindle sensory afferent nerves. The intrafusal muscle fibers 38 act on the afferent nerves 39 in the muscle spindles. The afferent nerves 39 send impulses to the central nervous system 30, and the alpha motor neurons 32 and the gamma motor neurons 36. Electrical stimulation 40 of the gamma motor neurons 36 modulates how the gamma motor neurons 36 act on the intrafusal fibers 38 and hence alters the sensitivity of the afferent neurons.

A decreased gamma motor neuron bias and will reset the muscle spindle sensory afferent neurons to a lower sensitivity. The high gain of the system will be decreased, and when an alpha motor neuron sends a signal (based on afferent input), to the extrafusal muscle fibers to contract the system will no longer be hypersensitized, and the motor neuron signal will result in an appropriate contraction, not an uncontrolled spasm. Thus, a low level of electrical stimulation provides a means of decreasing gamma motor neuron bias, thus utilizing electrical stimulation to decrease alpha motor neural activity and reduce spasm.

Figure 6:
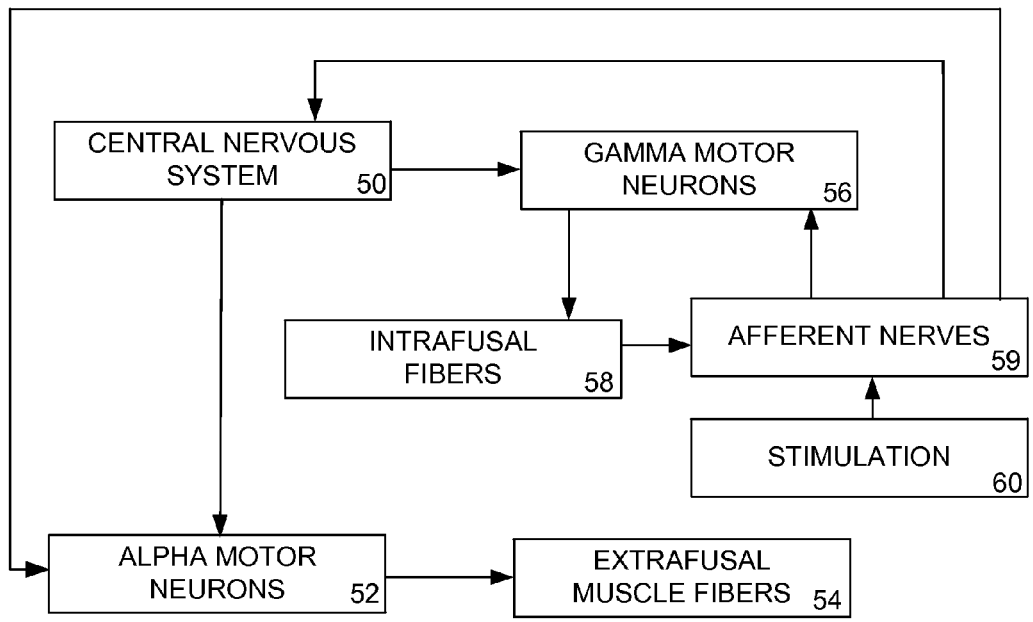
FIG. 6 is a flow chart illustrating the direction of impulses communicated between the central nervous system, the motor neurons, the muscles, the afferent nerves, and the gamma neurons and the impact of stimulation on the afferent system.

Further, as disclosed herein, electrical stimulation may alter the gamma motor loop by stimulating the afferent neurons, thus utilizing afferent nerve stimulation to alter abnormal alpha motor neuron activity to effectively reduce muscle spasm, as shown in FIG. 6. In the illustrated example, the central nervous system 50 sends impulses to alpha motor neurons 52, which fire, causing extrafusal muscle fibers 54 to contract. The central nervous system simultaneously sends impulses to the gamma motor neurons 56, which act on the intrafusal muscle fibers 58 of the muscle spindles. This coactivation of the gamma motor neurons 56 and the alpha motor neurons 52 maintains an appropriate level of sensitivity in the sensory afferent neurons of the muscle spindle. The intrafusal fibers act on the afferent nerves 59 innervating the intrafusal fibers 58 of the muscle spindle. These nerves send signals to the gamma and alpha motor neurons and the central nervous system 50. Stimulation of the afferent nerves innervating the intrafusal fibers 58 in the muscle spindles directly modulates the afferent-efferent loop, decreasing muscle spasm.

Low level stimulation, as disclosed herein, involves subjecting a sensory nerve or gamma motor neuron to an electrical impulse delivered by an electrode. The stimulating electrical impulse may vary by parameter such as duration, amplitude, frequency, and/or duty cycle. These parameters are set and governed using a processor which is operably connected with one or more electrodes which are used to administer the stimulating electrical impulse. The duty cycle is the duration of time in which an impulse is being delivered relative to the duration of time in which no impulse is being delivered. An interrupted, or non-continuous pattern of stimulation alternates periods of delivery of an impulse with periods in which no impulse is being delivered.

The duty cycle may be varied automatically by the processor. Additionally, the patient or individual directing treatment may turn the stimulator on or off as needed, resulting in an additional source of variation of stimulation. Without wishing to be bound by theory, the stimulation may be effective even when the stimulator is off because the sensory milieu has been altered.

Notably, low level stimulation as disclosed herein will only modulate action potentials associated with the muscle spindle, not block them, as blocking would result in significant laryngeal dysfunction. The approach of blocking action potentials associated with the muscle spindle has been described by Ayal et al. in U.S. Pat. No. 6,892,098 as a treatment for spasticity. Spasticity is found in conditions where the brain and/or spinal cord are damaged or fail to develop normally; these include cerebral palsy, multiple sclerosis, spinal cord injury and acquired brain injury including stroke. Damage to the CNS as a result of stroke or spinal cord injury alter the inhibition of peripheral nerves in the affected region by damaging the upper motor neuron. Damage to an upper motor neuron decreases its inhibitory function, resulting in over-activation of the alpha and gamma neurons. The decreased inhibition decreases action potential threshold for nerve signal conduction, and thus causes overactive motor neural activity, which in turn causes muscle spasm. Ayal proposes the use of electrical action potential blocking as a substitute source of inhibition. As taught by Ayal, a high frequency (600 Hz) current is driven into a nerve and travels toward the muscle being controlled, thus blocking body generated action potentials.

Action potential blocking as described by Ayal is unidirectional, requires high frequency stimulation, and prevents muscle movements by preventing/blocking sensory input to the central nervous system. Such an approach could not be utilized in the context of spasmodic dysphonia and is different than that described herein. First, SD is dystonia, is distinctly different from spasticity. Moreover, action potential collision blocking inhibits productive sensory inputs as well as abnormal sensory inputs. This can result in episodes of paralysis of laryngeal muscles whose precise movements are subtle and critical. As a result, action potential blocking could interfere with speech as well as swallowing and breathing. Hence, we have described herein an alternative method of stimulation that would avoid these potentially disastrous effects.

EXAMPLES

Example 1: Electrical Stimulation of the Thyroarytenoid Muscle (TA) Improves the Symptoms of SD This Example demonstrates that electrical stimulation of the thyroarytenoid muscle (TA) below threshold of alpha-motor neuron stimulation improves the symptoms of SD. Five subjects underwent daily stimulation of the left TA below the level of alpha-motor neuron activation for 5 consecutive days. Patients with SD who were previously responsive to BTX injections, aged between 18 to 75 years, and whose last BTX treatment was over 3 months ago were included. Patients on neuromodulating medication, with other neurological diseases, or with an implantable pacemaker were excluded.

Pretreatment laryngovideostroboscopy documented baseline vocal-fold function. A stainless steel bipolar hooked-wire electrode was placed into the left TA via the standard cricothyroid membrane approach. Electrical stimulation was set at 50 Hz with a pulse width of 200 microseconds (CareFusion, San Diego, Calif.). The amplitude of stimulation was increased until vocal fold twitching or increased tone was noted on laryngoscopy at 50 Hz or 3 Hz. The amplitude was then decreased until signs of motor stimulation were resolved (0.6-2.1 mA). This was performed each day. Subjects were stimulated for 1 hour.

Laryngovideostroboscopy was performed after the last stimulation and as needed to evaluate for alterations in vocal fold function. Prior to the first stimulation and after the last stimulation, subjects filled out a voice handicap index-10 (VHI). Before and after each stimulation session, subjects graded their level of dysphonia on a 5-point Liked scale.

They also read standardized sentences selected to stimulate adductor spasms. The sentences were repeated twice and digitally recorded over the telephone. The recorded sentences were sent in random order by a speech language pathologist (SLP) experienced in working with SD patients. The blinded SLP graded the level of SD on a 7-point Likert scale. The SLP also recorded the number of spasms in each sample. A spasm was defined as a phonatory break and did not include vocal strain (Table 1).

TABLE 1

Sentences Read by Subjects and Grading Scales Employed:

Sentences:
Please read the following sentences twice:
I eat apples and eggs.
Did he go to the right or to the left?
Early one morning a man and a woman were ambling along a one mile lane running near Rainy Island Avenue.
5-point Likert scale
Please rate your current level of dysphonia (circle one):
Mild - Mild/Moderate - Moderate - Moderate/Severe - Severe
7-point Likert scale
Rate the level of spasmodic dysphonia (circle one):
Normal - Mild - Mild/Moderate - Moderate - Moderate/Severe - Severe - Very Severe Four females and one male (subject 4) were recruited. No significant complications were noted. Laryngovideostroboscopy displayed normal vocal-fold function throughout the study. Two of five subjects displayed a yellow tinge to the vocal fold, suggesting a slight, insignificant hemorrhage.

Figure 7A:
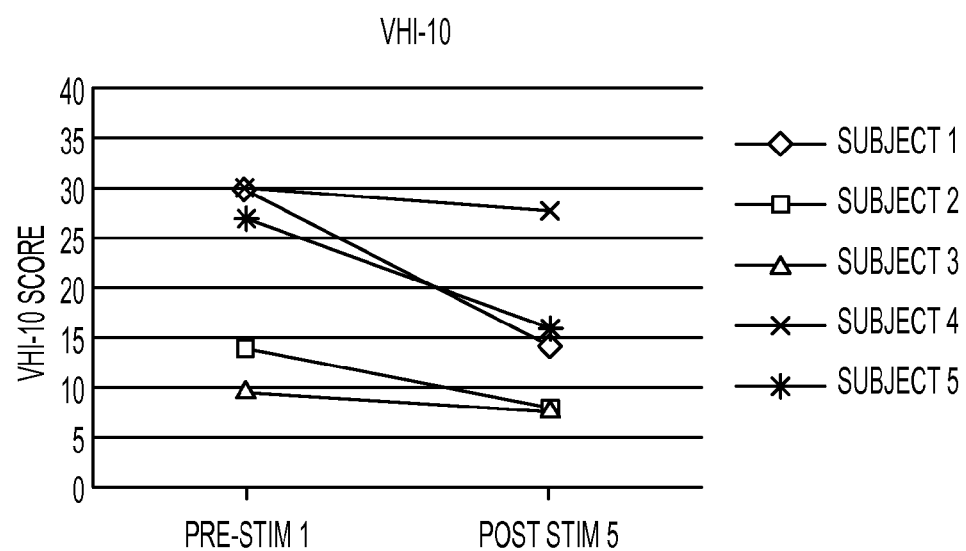
FIGS. 7A-7D are four graphs comparing a prestimulation score to the daily poststimulation scores of VHI-10 (FIG. 7A), spasm count (FIG. 7B), patient self voice evaluation (FIG. 7C), and expert voice evaluation (FIG. 7D)
Figure 7B:
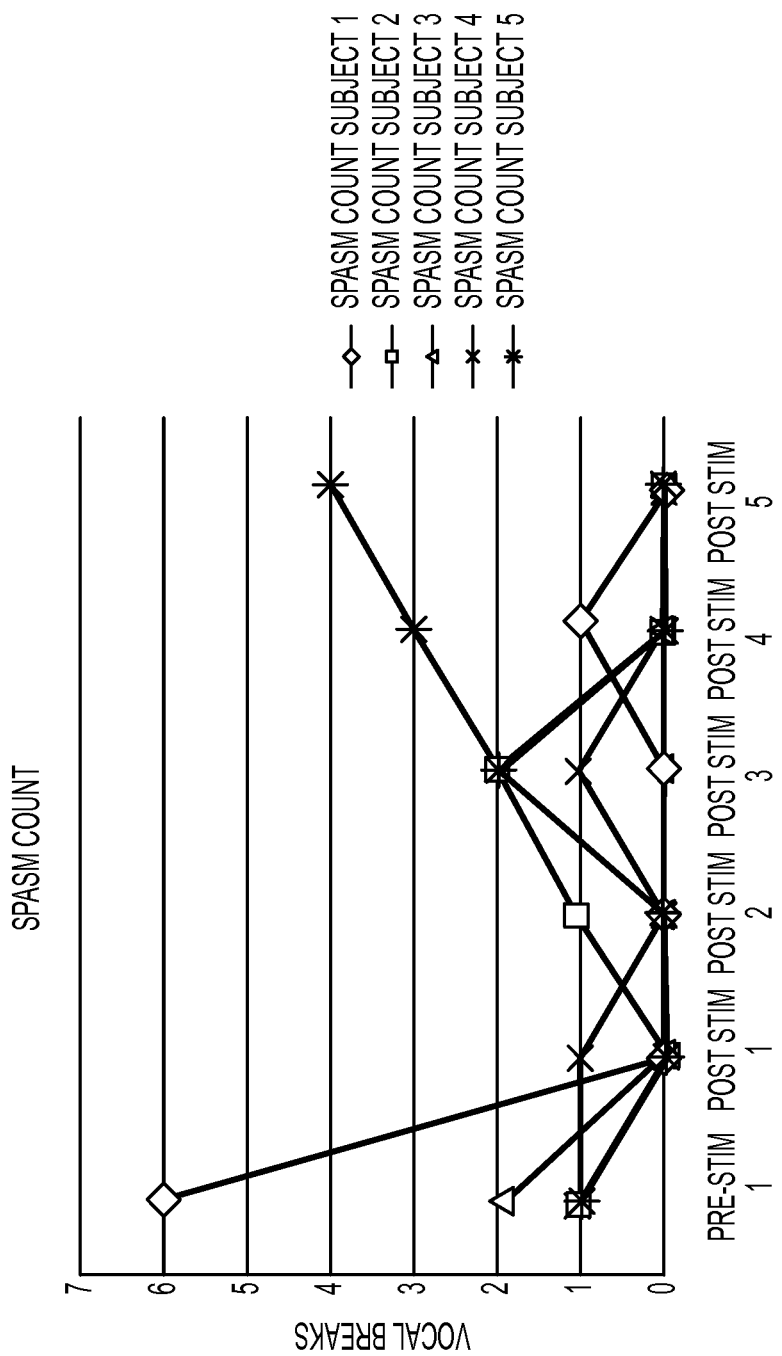
Figure 7C:
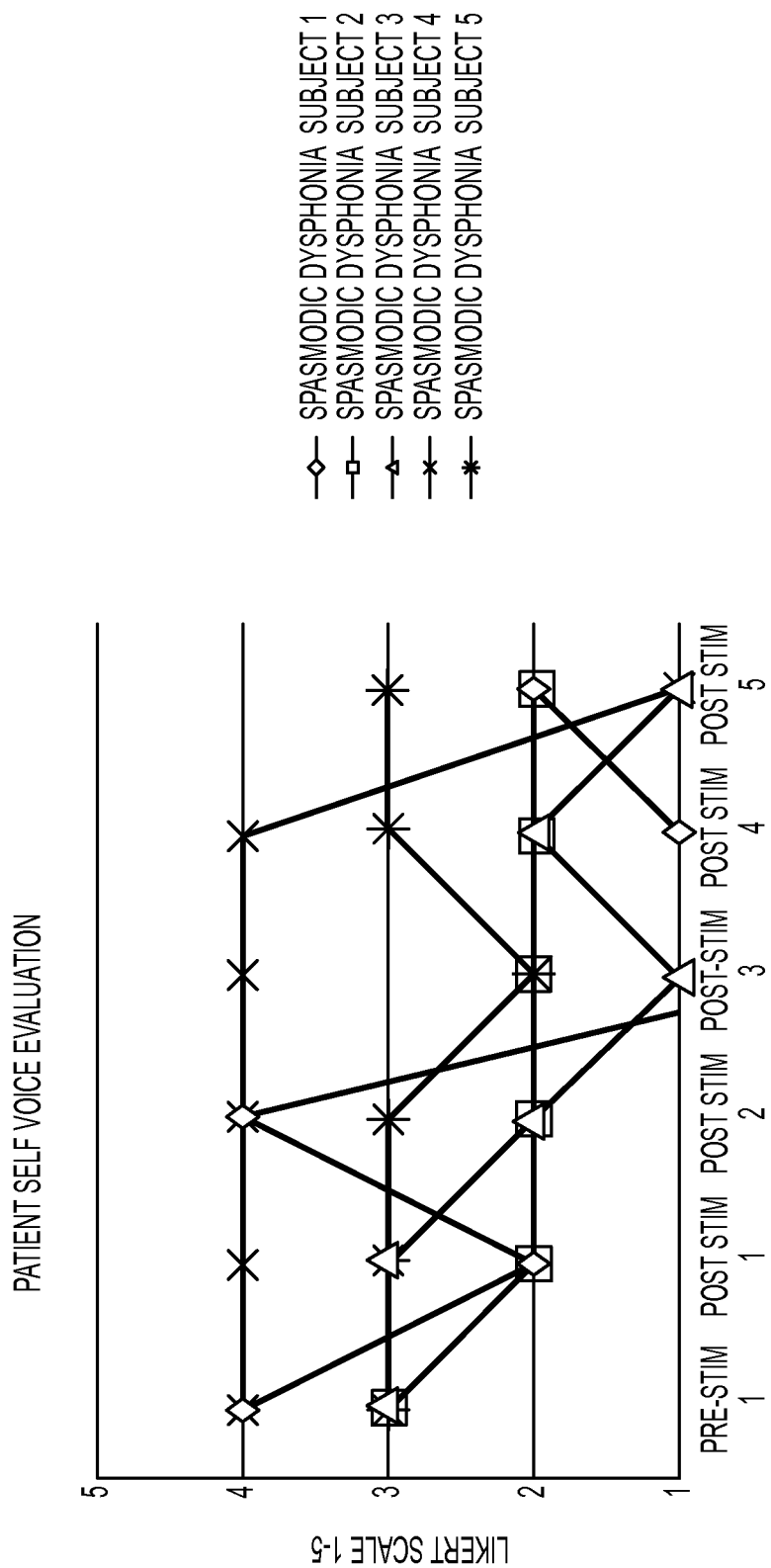
Figure 7D:
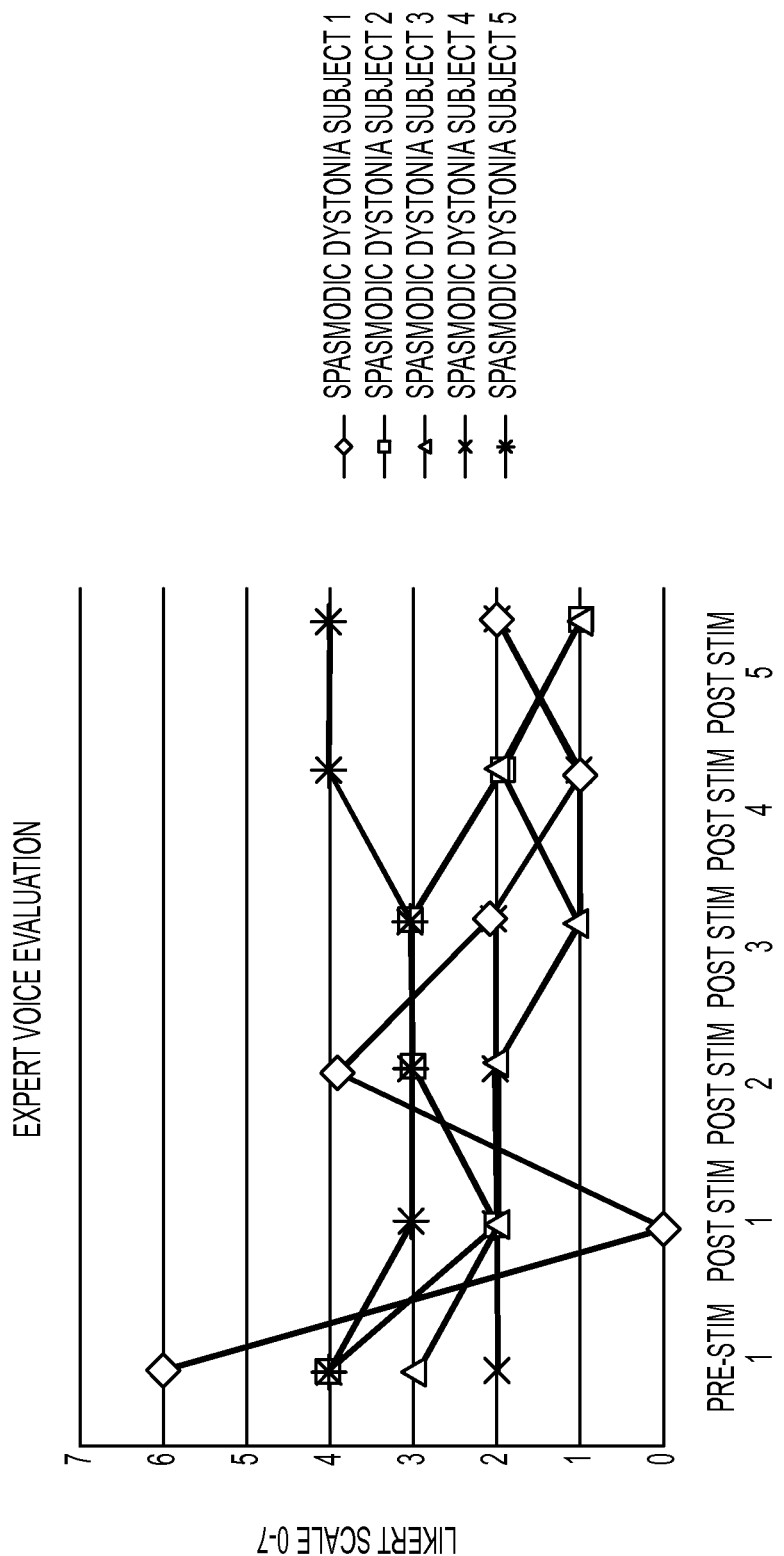

FIGS. 7A-7D are four graphs comparing a prestimulation score to the daily poststimulation scores of VHI-10 (FIG. 7A), spasm count (FIG. 7B), patient self voice evaluation (FIG. 7C), and expert voice evaluation (FIG. 7D), all in accordance with various embodiments. VHI-10 was scored only prestimulation and postfinal stimulation. The VHI improved in all subjects from prestimulation (PS) to the final poststimulation (FPS) with an average change of 7.4 (FIG. 7A). Spasm counts and subject self assessment of their SD symptoms decreased in all subjects from PS to FPS, except for subject 5 (FIG. 7B). This subject was improving until an upper respiratory infection (URI) developed on day 3. At this time, SD symptoms became more severe. Expert voice evaluation recorded improvement in three of five subjects PS to FPS (FIG. 7D).

Evaluation of FIGS. 7A-7D shows that improvement generally increased throughout the week. Although not specifically collected, subjects noted carryover of effect lasting 3 to 14 days, and a number of subjects reported their best voice in the afternoon after stimulation from 7 A.M. to 8 A.M. Subjects 1 and 3 felt that their voice was normal on days 4 and 3, respectively.

Figure 8A:
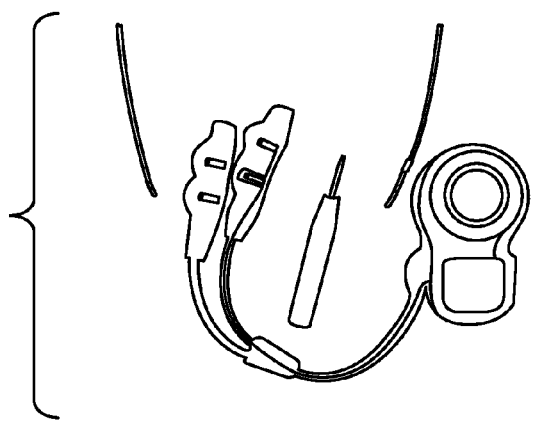
FIGS. 8A-8C illustrate an example of a bipolar stimulating system (FIG. 8A), an example of a stimulating trocar and cannula (FIG. 8B), and an example of a screwing mechanism at the end of a lead that fixes the lead into a target muscle (FIG. 8C)
Figure 8B:
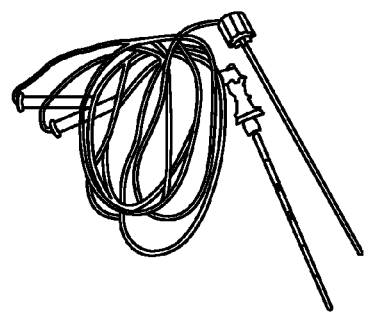
Figure 8C:
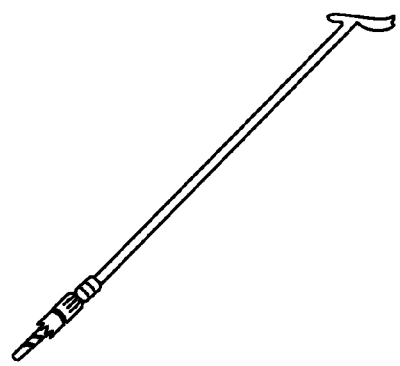

Example 2: Use of an Implantable Electrical Stimulation Device to Treat SD Via Neuromodulation of the Muscle Spindle Gamma Loop A domestic pig was placed under general anesthesia. A 3-cm incision was made over the thyroid cartilage, which was then exposed. Laryngoscopy was performed and the vocal folds were continuously visualized on a monitor. A system created for stimulation of the posterior cricoarytenoid muscle in the treatment of bilateral vocal-fold paralysis was employed (Med-El, Austria). FIGS. 8A-8C illustrate an example of a bipolar stimulating system (FIG. 8A), an example of a stimulating trocar and cannula (FIG. 8B), and an example of a screwing mechanism at the end of a lead that fixes the lead into a target muscle (FIG. 8C).

A trocar with stimulating tip was passed transcartilagenously into the TA. The stimulator was activated at 3 Hz (Neurosign, Carmarthenshire, UK). Placement within the TA was confirmed by vocal-fold adduction on stimulation. The probe was removed and the electrode lead was passed through the cannula into the TA, where it was screwed in place and fixed. The electrode was stimulated to confirm placement in the left TA, as described for the trocar. This procedure was performed twice. After the second insertion, the larynx was harvested and lead placement was visualized.

Leads were placed and successfully fixed in both trials. During placement of the second lead, the trocar initially violated the vocal fold mucosa. Although both trials resulted in stimulation, the first trial was more successful, with brisk and strong adduction, whereas the second was weak. After laryngeal harvest, the second lead placement was determined to be too posterior, fixed into tendinous attachments on the inferior aspect of the vocal process.

Example 3: Assessment of Whether the Electrode Lead is of Sufficient Length to Reach the Proposed Retroauricular Placement of the Stimulator In a fresh frozen cadaver, an electrode lead was passed into the left TA, simulating the method described above. The lead was affixed to the cartilage with a clasp, looped to create redundancy, and passed under the thyroid notch into the right neck. A trocar was passed in a subplatysmal plane from the incision to the mastoid tip. The lead was passed through the cannula and its position assessed.

The electrode lead was successfully passed in the subplatysmal plane from the larynx to the posterior neck just beneath the mastoid tip. The lead reached with length to spare and an absence of tension.

Example 4: Discussion—Use of an Implantable Electrical Stimulation Device to Treat SD Via Neuromodulation of the Muscle Spindle Gamma Loop BTX is the standard treatment for SD. This treatment is suboptimal due to discomfort and the need to be repeated frequently, as well as the significant time period of poor voice within each injection cycle. Considering this, a better treatment is necessary. As described herein, an alternative pathophysiology may be responsible for SD and for the function of BTX. As described herein, SD is not an isolated disorder of the basal ganglia. In contrast, cortical and cerebellar abnormalities have been elucidated in patients with SD, with the somatosensory cortex appearing to play a primary role in the pathophysiology of the disease. Accordingly, BTX injection results in significant changes in the cortex. Relative normalization of brain metabolism in the corticosensory areas is observed in SD patients on PET scans after injection.

These findings are in accordance with electromyographic recordings, which showed bilateral changes in the TA after unilateral BTX injection. Without being bound by theory, this alteration in peripheral neural activity likely is mediated via the central nervous system because its diffusion to the opposite vocal fold for local effect is improbable.

Without being bound by theory, it is likely that central changes observed after BTX injection are due to its effect on the muscle spindle. Vibration has been shown to trigger dystonia, and vibration-induced dystonia or action-induced dystonia may be mitigated by lidocaine injection or a sensory trick. Lidocaine is prone to blocking the gamma motor neuron and 1a afferent neuron of the muscle spindle, and the functional mechanism of sensory tricks is likely mediated by gamma inhibition, therefore the muscle spindle must play a primary role in dystonia. Additionally, BTX injection suppresses the tonic vibratory reflex, and this suppression persists beyond full return of muscle strength. This continued effect beyond that of muscle weakening indicates that BTX inhibition of the muscle spindle plays a significant role in its affect on dystonia.

Furthermore, after BTX treatment, intrafusal fibers of the muscle spindle atrophy in similar fashion to extrafusal fibers. Thus, without being bound by theory, the muscle spindle plays a principle role in dystonia, and the primary therapeutic pathway of BTX likely is on the muscle spindle via inhibition of acetylcholine release from the gamma motor neuron. Therefore, without being bound by theory, SD is not a motor disorder, but a sensory disorder with the primary effect of BTX being mediated through the inhibition of the gamma motor neuron that is innervating the intrafusal fibers of the muscle spindle.

Figure 9:
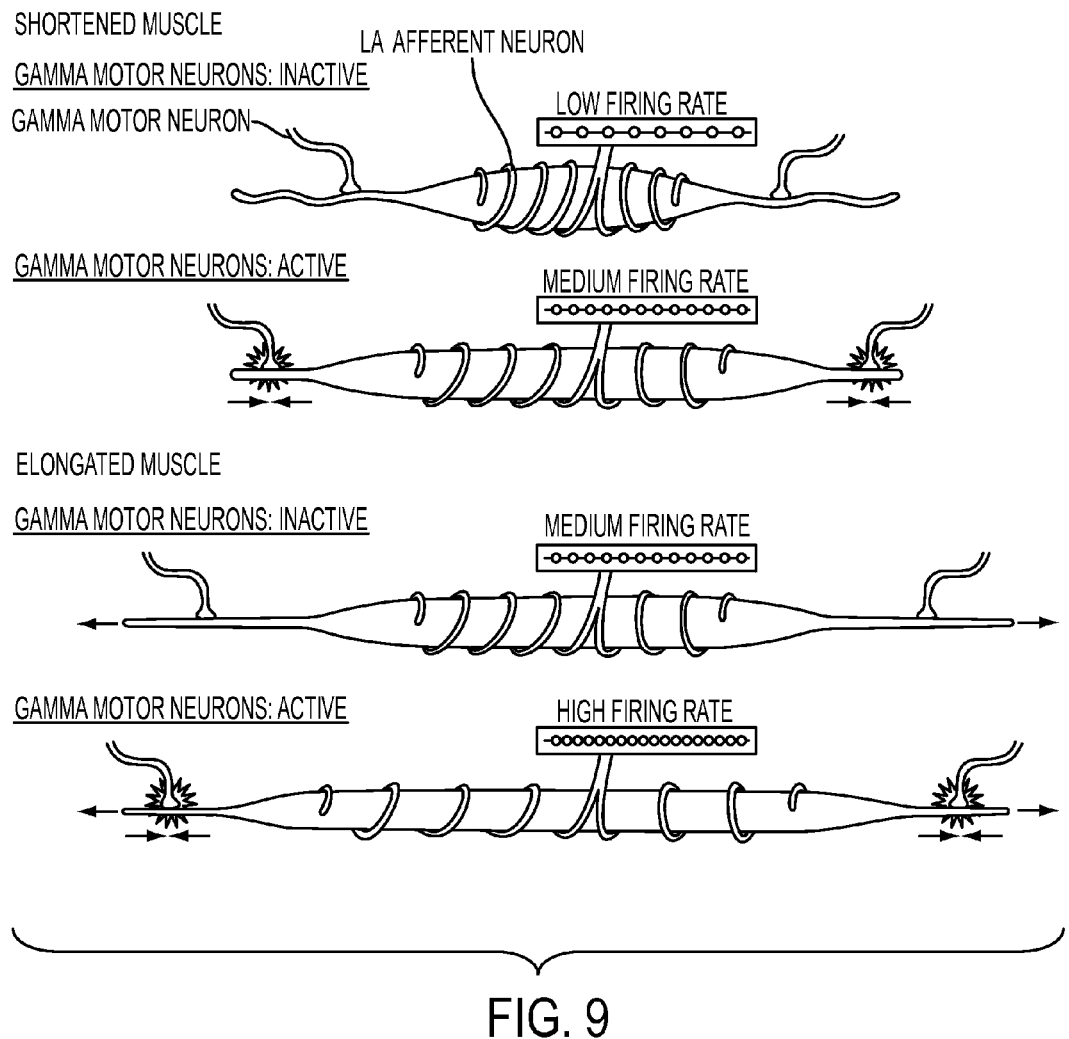
FIG. 9 illustrates how the gamma motor neuron regulates the sensitivity of the muscle spindle.
Figure 10:
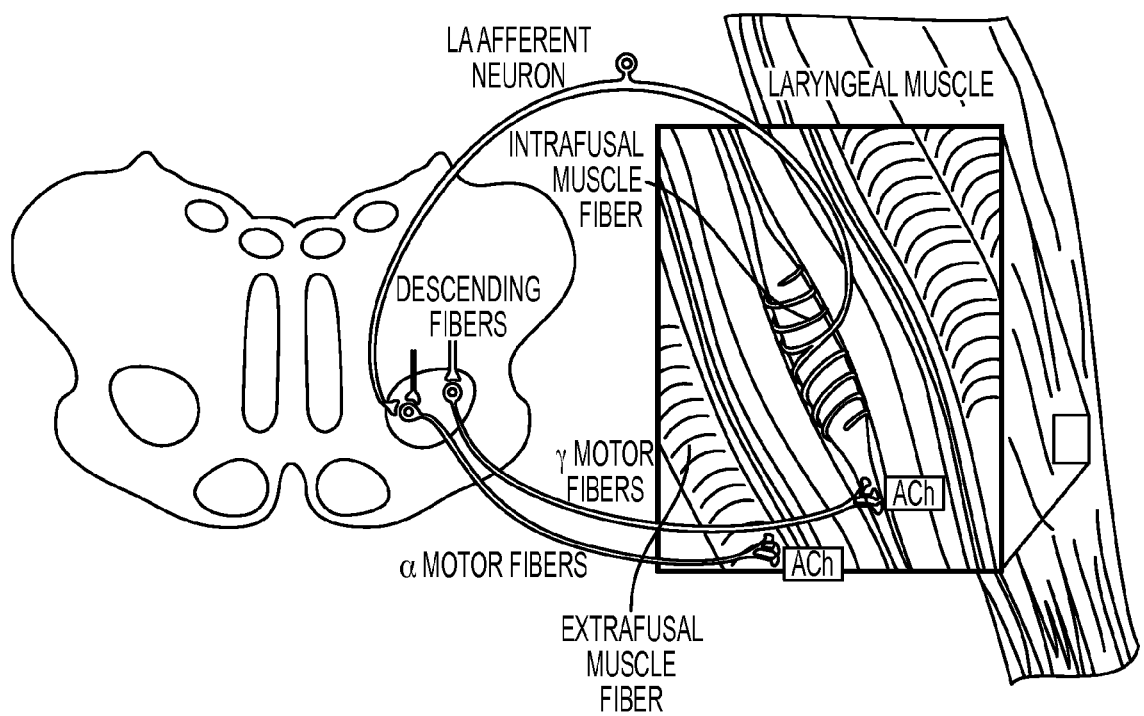
FIG. 10 illustrates the gamma loop with innervation of the muscle spindle intrafusial fiber and laryngeal muscle extrafusial fiber, all in accordance with various embodiments.

The muscle spindle is a sensory organ communicating muscle proprioception and velocity. The gamma motor neuron regulates the sensitivity of the muscle spindle. It keeps the intrafusal fibers of the muscle spindle taut so that the 1a afferent neuron can detect and transmit information on minute changes in extrafusial fiber tension. FIG. 9 illustrates how the gamma motor neuron regulates the sensitivity of the muscle spindlein accordance with various embodiments. Essentially, the gamma motor neuron sets the gain of the system. Gamma bias is the gamma motor neuron's consistent level of activity: low bias equals low gain, whereas high bias equals high gain. In SD, the gamma bias is too high. As a result, abnormal information is picked up by the 1 a afferent neuron and then transmitted to the central nervous system. This abnormal afferent information results in a rightfully abnormal alpha-motor neuron transmission to the extrafusial laryngeal muscle fibers that are producing a dystonic contraction with a vocal spasm. This system is referred to as the gamma loop. FIG. 10 illustrates the gamma loop with innervation of the muscle spindle intrafusial fiber and laryngeal muscle extrafusial fiber, in accordance with various embodiments.

Thus, as disclosed herein, electrical stimulation of the TA below threshold of alpha-motor neuron stimulation improves the symptoms of SD. All subjects in the present Examples manifested improvement in their voice, three of five in every outcome parameter. All subjects had improvement in their VHI and subject self-assessment: four of five subjects improved in spasm counts and three of five subjects improved in their expert voice evaluation. Subjects 1 and 3 felt that their voices was normal on days 4 and 3, respectively, prompting a change in the expert voice evaluation Liked scale to 7 points to include "normal." Although there is risk of placebo effect, the VHI and subject self-assessment may have been the most accurate in discerning the effect of treatment.

These measures reflected the subject's perception of their overall vocal function over a prolonged period during regular voice use. In contrast, the expert voice evaluation of dystonia severity and spasm counts were based on a review of a recording of three sentences read twice. These recordings provided a narrow sample and may not have fully represented changes in vocal function. In addition, as a whole, these grading systems are unrefined evaluators of SD response to treatment.

The parameters in which subjects did not improve included subject 4 in expert voice evaluation and subject 5 in a number of categories. The results for subject 5 are confounded due to the URI that was contracted on day 3. As often is observed with SD subjects, subject 5's dysphonia exacerbated with the onset of infection. It appeared that subject 5 had been improving. Her self-assessment score, expert voice evaluation, and spasm count initially decreased. The post-VHI, which was improved by nine points, may reflect this early improvement. Subjects 1 through 4 appeared to improve throughout the week as if there was an additive effect to the treatment. On a number of occasions, subjects also noted that their best voice was not immediately after stimulation, which occurred from 7 A.M. to 8 A.M., but in the afternoon. Subjects 1 through 4 all noted a carryover of effect from 3 to 14 days after the last stimulation.

Without being bound by theory, it is likely that the sub-alpha-motor neuron stimulation that was performed here exerted its effect by modulating the muscle spindle gamma loop via inhibition of the gamma motor neuron. Without being bound by theory, the effect may also have been via neuromodulation of the 1a afferent nerve.

In contrast to a blindly placed hooked-wire electrode, controlled placement of a multichannel electrode within the TA will improve the ability to neuromodulate a larger number of the gamma loop-related neurons. The position of the stimulation, as well as its parameters, may be optimized, as is done when a multichannel cochlear implant is mapped. Once mapped, SD patients are able treat themselves as needed, turning on the stimulator by affixing a magnetized transcutaneous battery to it. Treatment would be intermittent.

Better stimulation technology may be provided in the form of the stimulator shown in FIGS. 8A-8C (Med-El, Austria). This implantable device has been successfully implanted in eight human patients (Med-El). As shown herein, the current model allows for fixation of the lead in the TA with successful muscle stimulation. The lead also passes easily in a subplatysmal plane from the larynx to the mastoid area.

Thus, as shown herein, the symptoms of SD improve after electrical stimulation of the left TA at levels below alpha-motor neuron activation. Without being bound by theory, the effect is likely via neuromodulation of the spindle gamma loop that is mediated through affect on the gamma-motor neuron—and possibly on the 1a afferent neuron. Placement of an electrode into the TA with a postauricular stimulator is feasible with modifications of an already existing device. Thus, this implantable device delivers a painless self administered treatment as an alternative to BTX.

Example 5: Direct Stimulation of the Superior Laryngeal Nerve to Treat SD Via Neuromodulation of the Muscle Spindle Gamma Loop In this example, the superior laryngeal nerve (SLN) is stimulated directly in order to treat SD. The method requires the surgical implantation of a stimulator device, such as using a retroauricular placement similar to a cochlear implant (CI), with the electrical lead passing into the neck instead of the round window. An implantable neurostimulatory device is used that, in some examples, may include a titanium-encased generator with a lithium battery to fuel the generator, or an external (not-implanted) battery powering the implanted generator by an inductive link, similar to that used with a cochlear implant (CI), a lead wire system with electrodes, and an anchor tether to secure leads to the superior laryngeal nerve. The battery life for the pulse generator may be up to 16 years or more, depending on the settings (e.g., signal strength, the length of time the device stimulates the nerve each time, and how frequently the device stimulates the nerve), or a rechargeable battery may be used instead.

Implantation of the neurostimulatory device may be performed as an outpatient procedure. An exemplary procedure is as follows. The subject is placed under general anesthesia, an incision is made in a suitable location, such as the upper left chest or the retroauricular space (similar to that used with a cochlear implant), and the generator is implanted into a "pouch" under the skin. An incision of about 3 cm is then made over the thyroid cartilage, which is then exposed. Laryngoscopy is performed and the vocal folds may be continuously visualized on a monitor.

A trocar with stimulating tip is then passed transcartilagenously to the superior laryngeal nerve. The surgeon then wraps the lead(s) around the superior laryngeal nerve or places the electrode in direct electrical or physical contact with the superior laryngeal nerve or a branch thereof and connects the electrodes to the generator. Once successfully implanted, the generator sends electric impulses to the superior laryngeal nerve at regular intervals or as needed. The stimulator initially may be activated at about 1-3 Hz to verify that the electrode is placed appropriate to activate the superior laryngeal nerve. Placement on the SLN is confirmed by vocal-fold adduction on stimulation. The probe is then removed and the electrode lead is passed through the cannula to the SLN, where it is fixed in place with a commercially available nerve cuff. The electrode is then stimulated to confirm placement on the SLN, as described for the trocar.

Specific, non-limiting examples of neurostimulatory devices that may be used include those made by Cyberonics, Inc., Houston, Tex. and Neurosign, in Carmarthenshire, UK. In some examples, a commercially available nerve cuff is used to couple the lead(s) to the superior laryngeal nerve. Nerve cuffs may take any of several different forms, such as spiral cuffs, tripolar cuffs, concentric cuffs, and the like. Suitable nerve cuffs are available from MicroProbes, in Gaithersburg, Md., World Precision Instruments, in Sarasota, Fla., and Ardiem Medical, in Indiana, Pa.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of treating spasmodic dysphonia in a subject, comprising:
    providing a system comprising a stimulating electrode operably connected with a processor configured to set one or more stimulation parameters for an electrical impulse deliverable by said electrode;
    placing said electrode in electrical contact with the superior laryngeal nerve;
    using the processor to set the stimulation parameters such that the electrical impulse causes a level of stimulation that does not exceed the excitability threshold of one or more alpha motor neurons located within the thyroarytenoid muscle; and
    delivering the electrical impulse to the superior laryngeal nerve; wherein the electrical impulse decreases a level of activity of one or more gamma motor neurons.

2. The method of claim 1, wherein placing said electrode in electrical contact with the superior laryngeal nerve comprises applying a nerve cuff to the superior laryngeal nerve.

3. The method of claim 1, wherein the electrical impulse has an amplitude, a frequency, and a duty cycle governed by parameters set by the processor, and wherein at least one of the amplitude and the frequency and the duty cycle are varied during a treatment.

4. The method of claim 1, wherein the electrical impulse decreases a level of activity of one or more afferent neurons.

5. The method of claim 1, wherein the stimulating electrical impulse inhibits at least one neural signal transmitted to a central nervous system by one or more afferent neurons.

6. A method of treating spasmodic dysphonia in a subject, comprising:
    using an electrode in communication with a processor to deliver an electrical impulse to a neuron in a superior laryngeal nerve, wherein the impulse delivers a level of stimulation that is below an excitability threshold of one or more alpha motor neurons innervating a thyroarytenoid muscle in the subject, wherein the electrical impulse decreases a level of activity of one or more afferent neurons, and
    delivering the electrical impulse to the superior laryngeal nerve; thereby treating spasmodic dysphonia in the subject.

7. The method of claim 6, wherein the electrode is placed in electrical contact with the superior laryngeal nerve.

8. The method of claim 7, wherein the electrode is placed in electrical contact with the superior laryngeal nerve via a nerve cuff.

9. The method of claim 6, wherein the electrical impulse has an amplitude, a frequency, and a duty cycle governed by parameters set by the processor, and wherein at least one of the amplitude and the frequency and the duty cycle are varied during a treatment.

10. The method of claim 6, wherein the electrical impulse decreases a level of activity of one or more gamma motor neurons.

11. The method of claim 6, wherein the electrical impulse alters or inhibits at least one neural signal transmitted to a central nervous system by one or more afferent neurons.

12. A system for treating spasmodic dysphonia in a subject, comprising an electrode configured to deliver an electrical impulse to a superior laryngeal nerve, the electrode being in communication with a processor configured to set one or more stimulation parameters governing the electrical impulse, wherein the processor causes the electrical impulse to deliver a level of stimulation to a nerve placed in communication with the electrode, said level of stimulation being below an excitability threshold of one or more alpha neurons innervating a thyroarytenoid muscle in the subject; wherein the electrical impulse acts upon one or more gamma neurons located within the thyroarytenoid muscle.

13. The system of claim 12, wherein the electrical impulse has an amplitude, a frequency, and a duty cycle governed by the parameters, and wherein at least one of the amplitude and the frequency and the duty cycle are varied during a treatment.

14. The system of claim 12, wherein the electrical impulse acts upon one or more muscle spindles located within the thyroarytenoid muscle.

15. The system of claim 12, wherein the electrical impulse decreases a level of activity of the one or more gamma neurons.

16. The system of claim 12, wherein the electrical impulse acts upon one or more afferent neurons located within the thyroarytenoid muscle.

17. The system of claim 16, wherein the electrical impulse decreases a level of activity of the one or more afferent neurons.

18. The system of claim 16, wherein the electrical impulse inhibits at least one neural signal transmitted to a central nervous system by the one or more afferent neurons.

* * * * *